US00PP35167P3

(12) United States Plant Patent
Tufaro

(10) Patent No.: US PP35,167 P3
(45) Date of Patent: May 16, 2023

(54) STRAWBERRY PLANT NAMED 'NSG 465'

(50) Latin Name: ***Fragaria* x *ananassa* Duchesne**
Varietal Denomination: NSG 465

(71) Applicant: Nova Siri Genetics SRL, Policoro (IT)

(72) Inventor: Nicola Tufaro, Nova Siri (IT)

(73) Assignee: NOVA SIRI GENETICS SRL, Policoro (IT)

( * ) Notice: Subject to any disclaimer, the term of this patent is extended or adjusted under 35 U.S.C. 154(b) by 0 days.

(21) Appl. No.: 17/832,239

(22) Filed: Jun. 3, 2022

(65) Prior Publication Data

US 2022/0394901 P1 Dec. 8, 2022

(30) Foreign Application Priority Data

Jun. 7, 2021 (QZ) ..... PBR 20211459

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208
CPC ... A01H 5/08; A01H 5/02; A01H 5/00; A01H 6/74; A01H 6/7409
See application file for complete search history.

*Primary Examiner* — June Hwu
(74) *Attorney, Agent, or Firm* — Buchanan Ingersoll & Rooney P.C.

(57) ABSTRACT

A new and distinct variety of strawberry plant, referred to by its cultivar name, 'NSG 465', is provided which exhibits a semi-dense habit and a semi-upright to spreading growth. 'NSG 465' displays, on an early basis, white inflorescence generally at the same level of the foliage. 'NSG 465' commonly displays a calyx that is much larger than the diameter of its corolla when open. 'NSG 465' forms in abundance medium-ripening attractive fruits of large dimensions, moderately longer in length than in width, mainly conical, with very firm flesh and medium red color. The new variety is particularly well suited for the commercial industry.

12 Drawing Sheets

Figure 1:
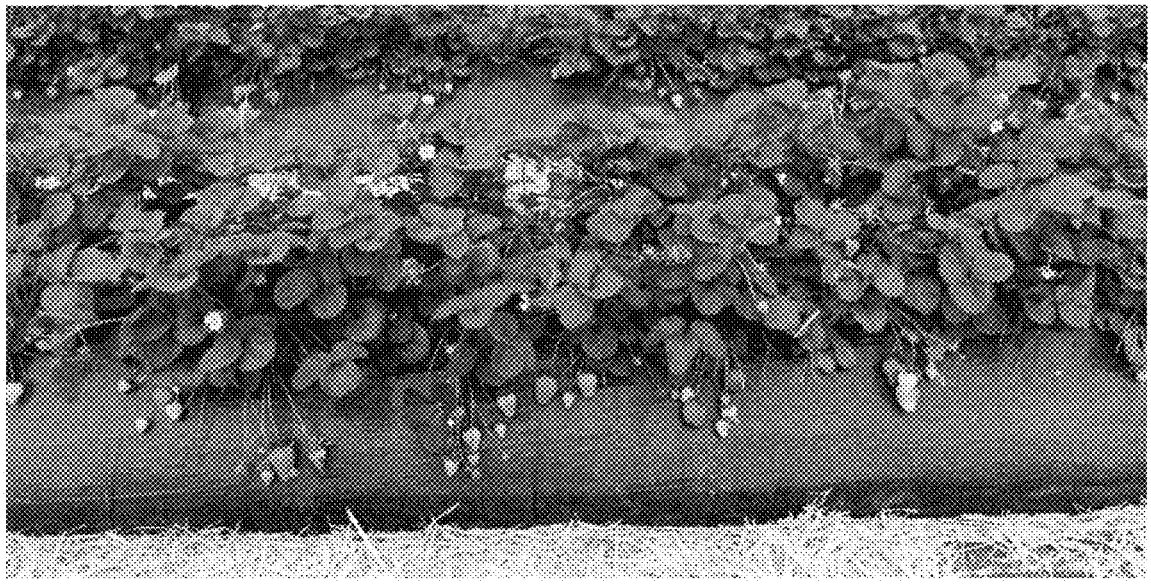

Botanical/commercial classification:
Latin name: *Fragaria* x *ananassa* Duchesne.
Varietal denomination: 'NSG 465'.

CROSS-REFERENCE TO RELATED APPLICATIONS

This application claims priority to Community Plant Variety Rights Application Number 2021/1459 which was filed in European Union through Community Plant Variety Office on Jun. 7, 2021, of which the content of is hereby expressly incorporated by reference in its entirety for all purposes.

SUMMARY OF THE INVENTION

The new and distinct short-day strawberry plant variety of the present invention was the product of a controlled breeding program that was carried out in Policoro (MT) Italy located at 40° 197 N-16° 656 E, wherein two parents were crossed which previously had been studied in the hope that they would contribute the desired characteristics. The female parent (i.e., the seed parent) was the 'SIRIS' variety (non-patented in the United States and European Union Community Plant Variety Rights No. 34843), which is a strawberry variety plant with medium late-season yield and produces fruit with very high contents of sugar and exhibits high tolerance to infection by fungus, such as *Phytophthora cactorum* and *Colletotrichum acutatum*. The male parent (i.e., pollen parent) was the 'NSG 120' variety (U.S. Plant Pat. No. 32,192 P3 and European Union Community Plant Variety Rights No. 57092), which is a strawberry variety that produces a high quality of fruits and sugar during the whole harvest cycle.

The parentage can be summarized as follows:

'SIRIS' x 'NSG120'.

The seeds resulting from the above pollination were sown and small plants were obtained which were physically different from each other. Selective study and testing resulted in the identification of a single short-day strawberry plant of the new variety. It was found that the new strawberry plant of the present invention possesses the following combination of characteristics:

(a) exhibits a semi-dense habit and a semi-upright to spreading growth,
(b) displays, on an early basis, white inflorescence, generally, at the same level of the foliage,
(c) commonly displays a calyx that is much larger than the diameter of the corolla when open,
(d) forms in abundance medium-ripening attractive fruits of large dimensions, moderately longer in length than in width, mainly conical, with very firm flesh and medium red color.

The new variety well meets the needs of the horticultural industry. The new variety possesses characteristics that commonly are sought by commercial strawberry growers. For example, the new variety provides uniform attractive firm medium red, medium-ripening fruit in good yields. The new variety requires an induction period for flowering. This may be achieved by growing in a colder climate away from the equator or at a higher altitude above sea level.

The new variety can be readily distinguished from its ancestors. More specifically, the 'SIRIS' variety (i.e., the seed parent) displays generally cordate shape fruit, with orange red internal color and a white core. Instead, the fruit of the new variety, is conical with the internal color and the core of a medium red. The diameter of the calyx of 'SIRIS' is much smaller than the diameter of the fruit, while in the new variety the diameter of the calyx is larger than the diameter of the fruit. In addition, the variety 'NSG 120' (i.e., the pollen parent) has the insertion of the calyx above the level of the fruit and its diameter is slightly larger than the diameter of the fruit, which has an absent or very small cavity. In the new variety, instead, the insertion of the calyx is on the same level of the fruit and the diameter of the calyx is much larger as compared to the diameter of the fruit, which has a medium cavity. Furthermore, 'NSG 120' shows an upright to semi-upright habit with the flowering above the level of the foliage, while in the new variety the habit is semi-upright to spreading with the flowering on the same level of the foliage. The terminal leaflets in 'NSG 120' are moderately longer in length than width, possess a crenate margin and an acute base, while the leaflets of the new variety have commonly the same dimension in width and length, possesses a serrate-to-crenate margin, and an obtuse base.

Moreover, the new variety can be readily distinguished from non-parental related similar varieties. For example, the 'NSG 207' variety (U.S. Plant Pat. No. 32,161 P3 and European Union Community Plant Variety Rights No. 57091) exhibits an upright habit and the position of the flowering is above the level of the foliage, provides fruit with external red orange color and internal light red, has a calyx with a diameter that is the same dimension as the diameter of the fruit, which has an absent or very small cavity. On the contrary, the new variety has a habit that is semi-upright to spreading, has a position of flowering that is on the same level as the fruit, has fruit that is conical with an external medium red color, has a calyx with a diameter that is much larger than the diameter of the fruit, which has a medium cavity. Compared to the new variety, 'NSG 207' has leaves with an acute base while the leaflets of the new variety commonly have leaves with an obtuse base.

The new variety has been found to undergo asexual propagation in Spain and Italy by a number of routes, including by use of stolons and in vitro tissue culture. Specifically, the new variety has been asexually reproduced in a nursery setting by the use of stolons in TORDESILLAS, Spain, located at 41° 494 N-4° 908 E and in Policoro, Italy, by in vitro tissue culture. No rotting problems were observed on the roots during cultivation. The combination of characteristics exhibited by the new variety has been found to be stable and reliably transmitted to succeeding generations following such asexual reproduction. Accordingly, the new variety undergoes asexual propagation in a true-to-type manner by such asexual reproduction.

BRIEF DESCRIPTION OF THE PHOTOGRAPHS

The accompanying photographs show, as nearly true as it is reasonably possible to make the same in color illustrations of this character, typical specimens of the new variety identified by the code s20.n.17-465 (breeder reference). The illustrated strawberry plants of the new variety were asexually reproduced by stolons in a nursery at TORDESILLAS, Spain, 41° 494 N-4° 908 E, and were planted under the cover of plastic tunnels during mid October 2021 in Policoro (MT) located at 40° 197 N-16° 656 E, Italy.

FIG. 1—illustrates a row of fruiting plants in May 2022, wherein the flowering is at the same level of the foliage.

Figure 2:
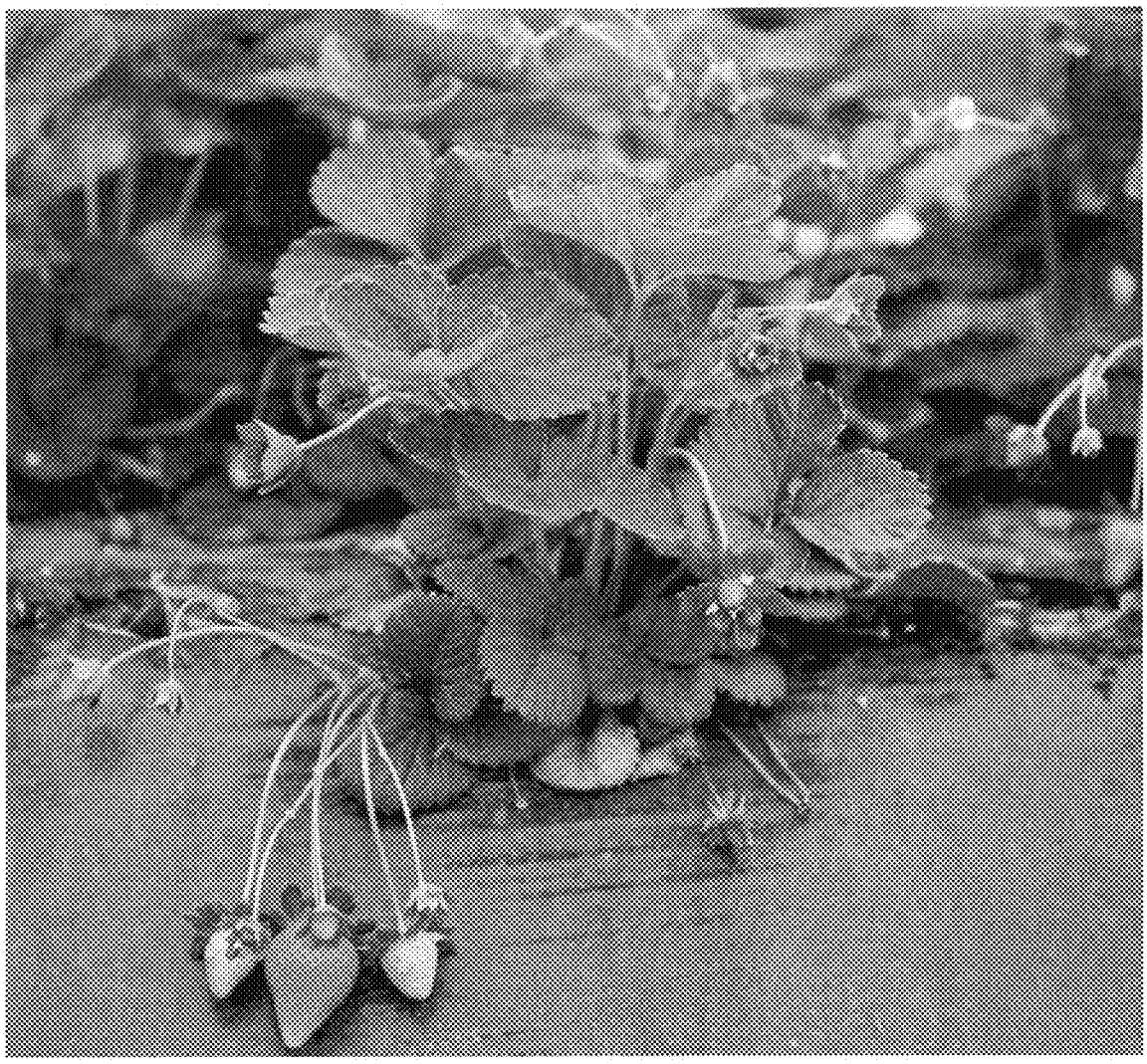

FIG. 2—illustrates the plant variety with its semi upright to spreading habit and medium vigor.

Figure 3:
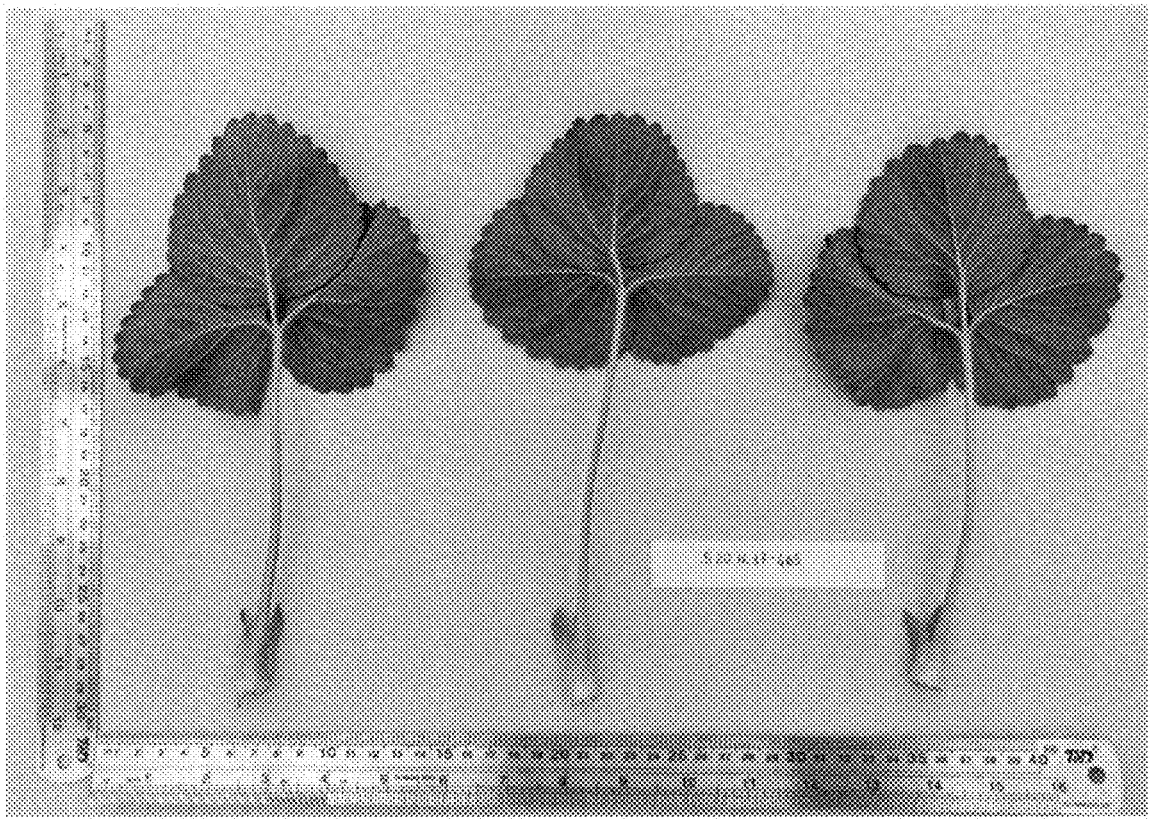

FIG. 3—illustrates specimens of the new variety's three-leaflet leaves—under surface, wherein the petiole and stipules are further apparent. Dimensions in centimeters and inches are included.

Figure 4:
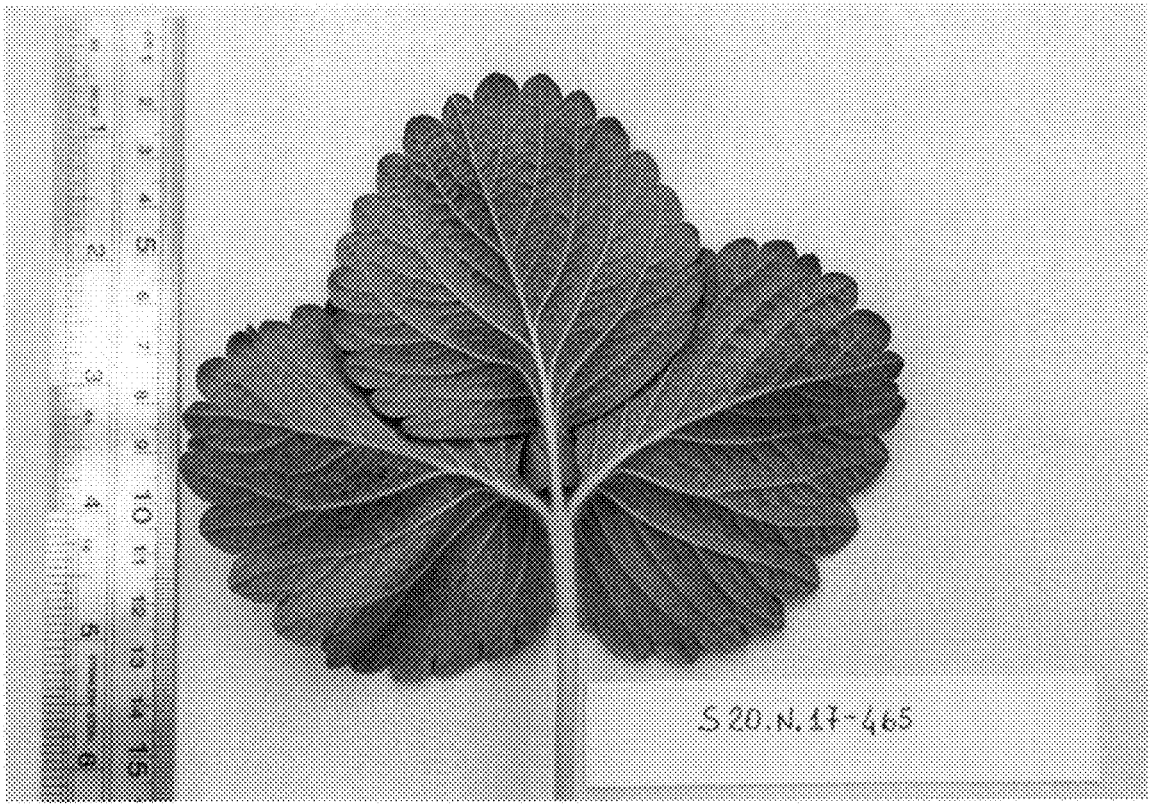

FIG. 4—illustrates specimens of the new variety's three-leaflet leaves—under surface, in particular the leaf veins. Dimensions in centimeters and inches are included.

Figure 5:
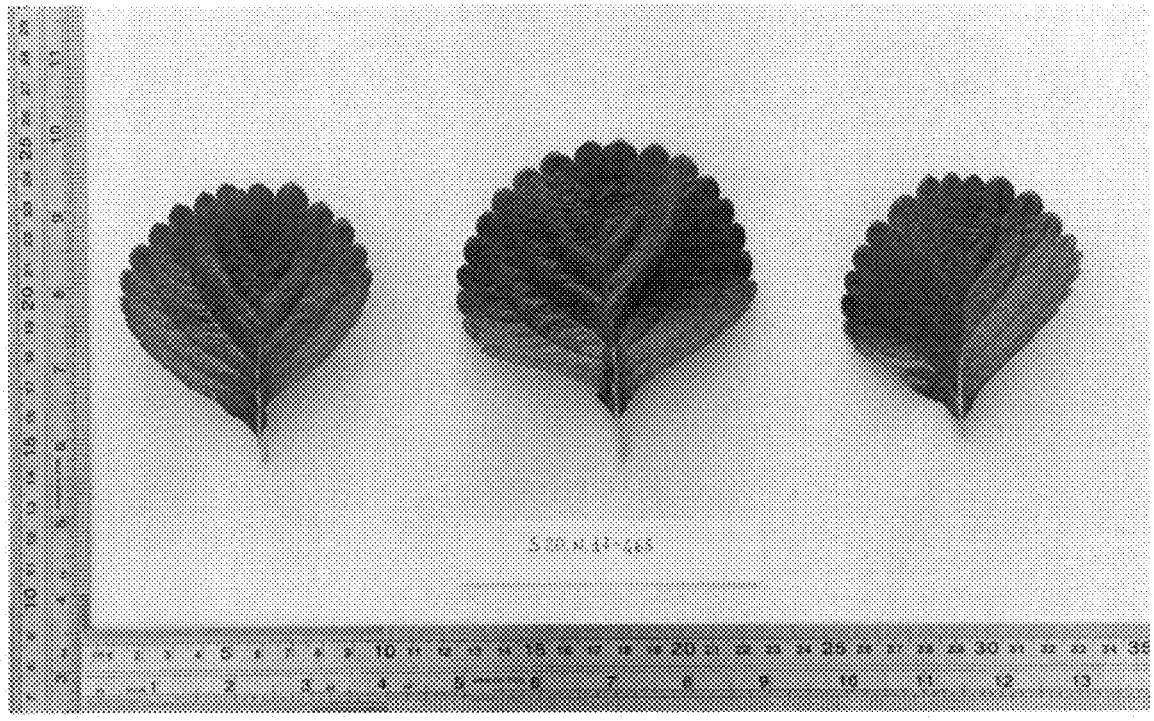

FIG. 5—illustrates the upper surface of the new variety's terminal leaflet.

Figure 6:
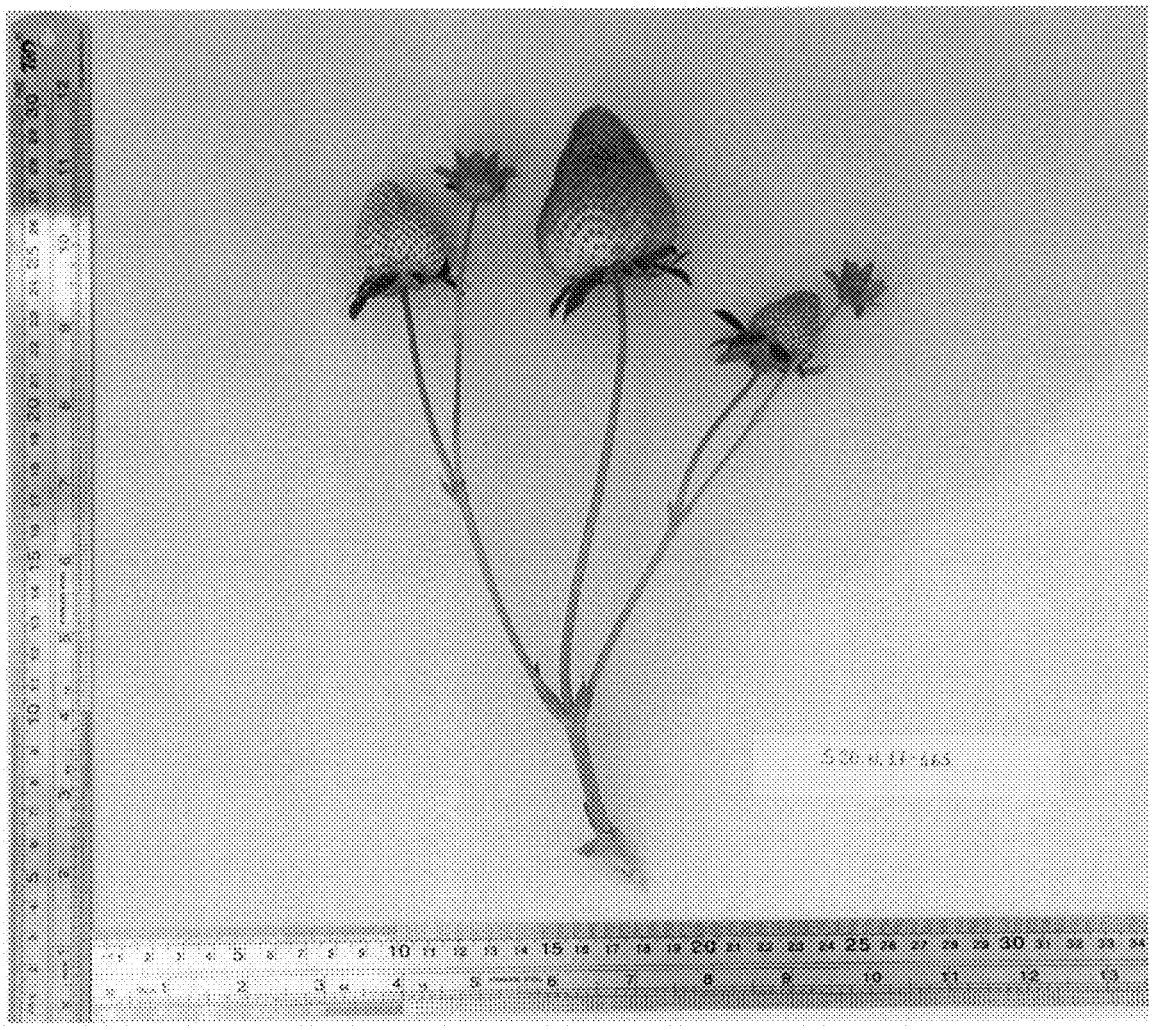

FIG. 6—illustrates a fruiting specimen of the new variety. Dimensions in centimeters and inches are included.

Figure 7:
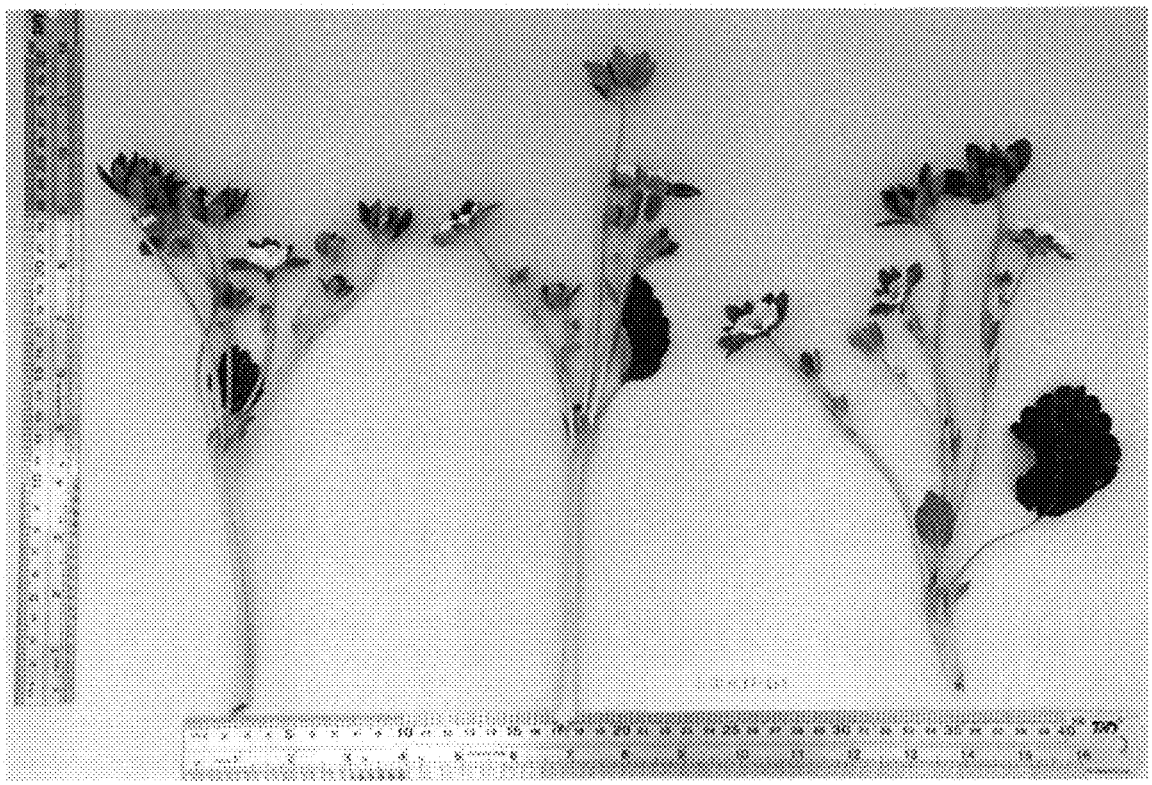

FIG. 7—illustrates a flowering specimen of the new variety. Dimensions in centimeters and inches are included.

Figure 8:
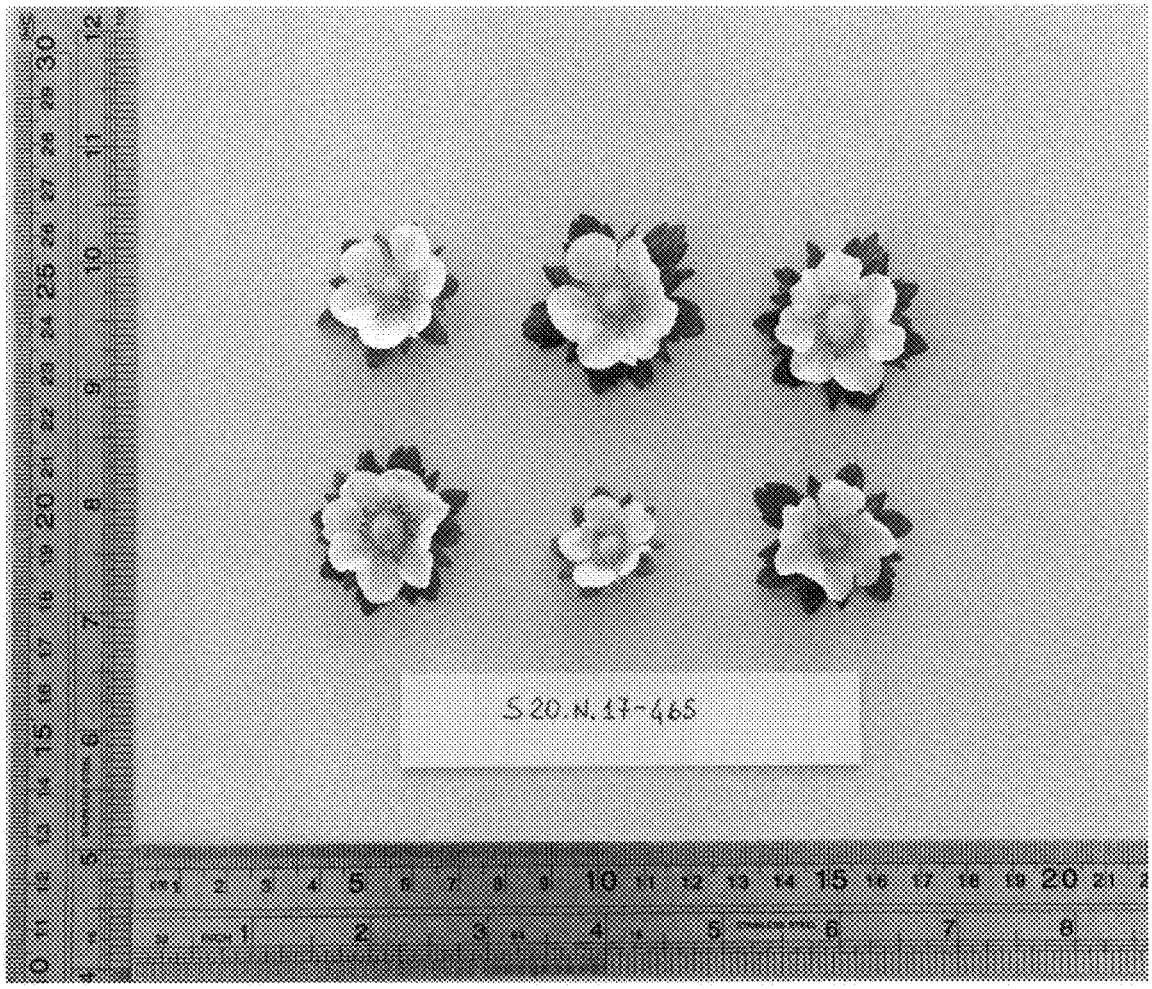

FIG. 8—illustrates flowers of the new variety, view from above. Dimensions in centimeters and inches are included.

Figure 9:
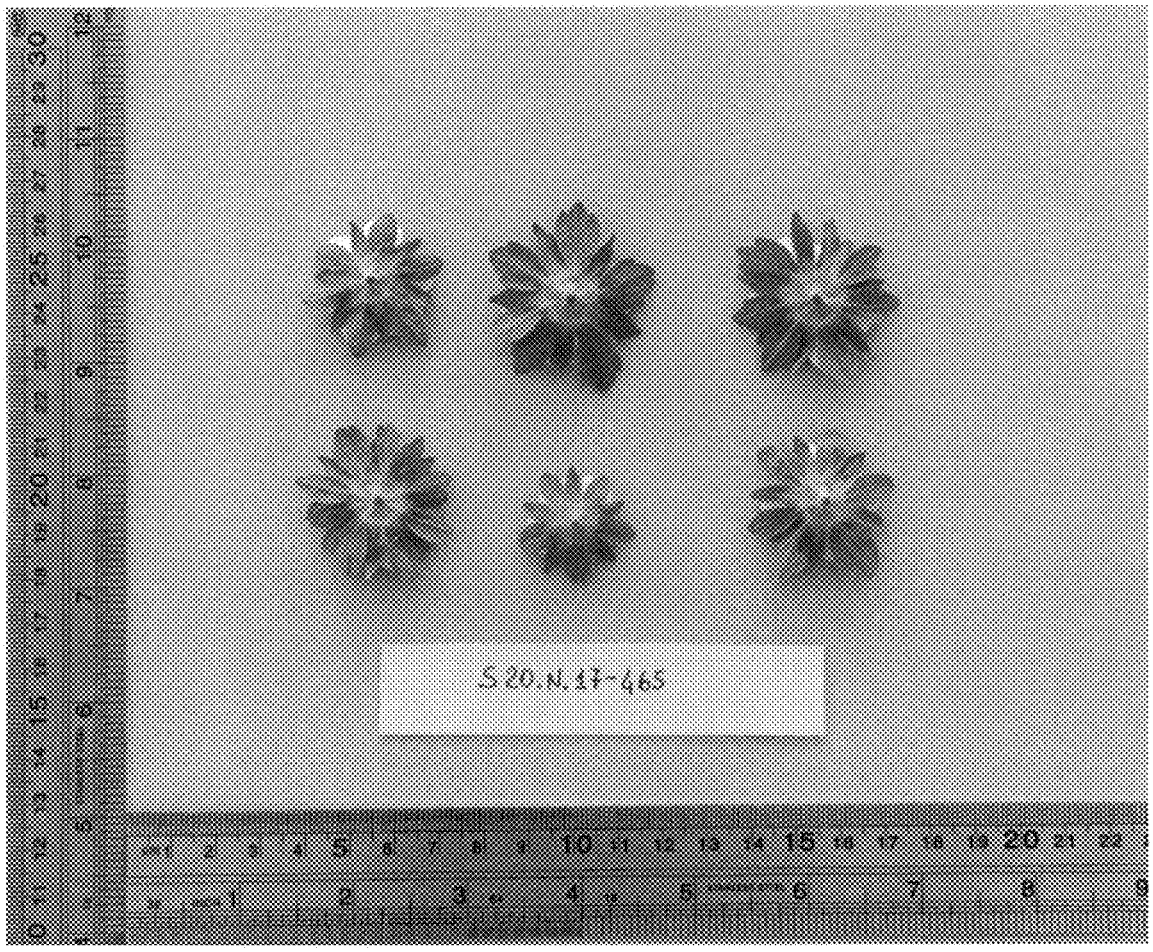

FIG. 9—illustrates specimens of the new variety's calyx, view from above. Dimensions in centimeters and inches are included.

Figure 10:
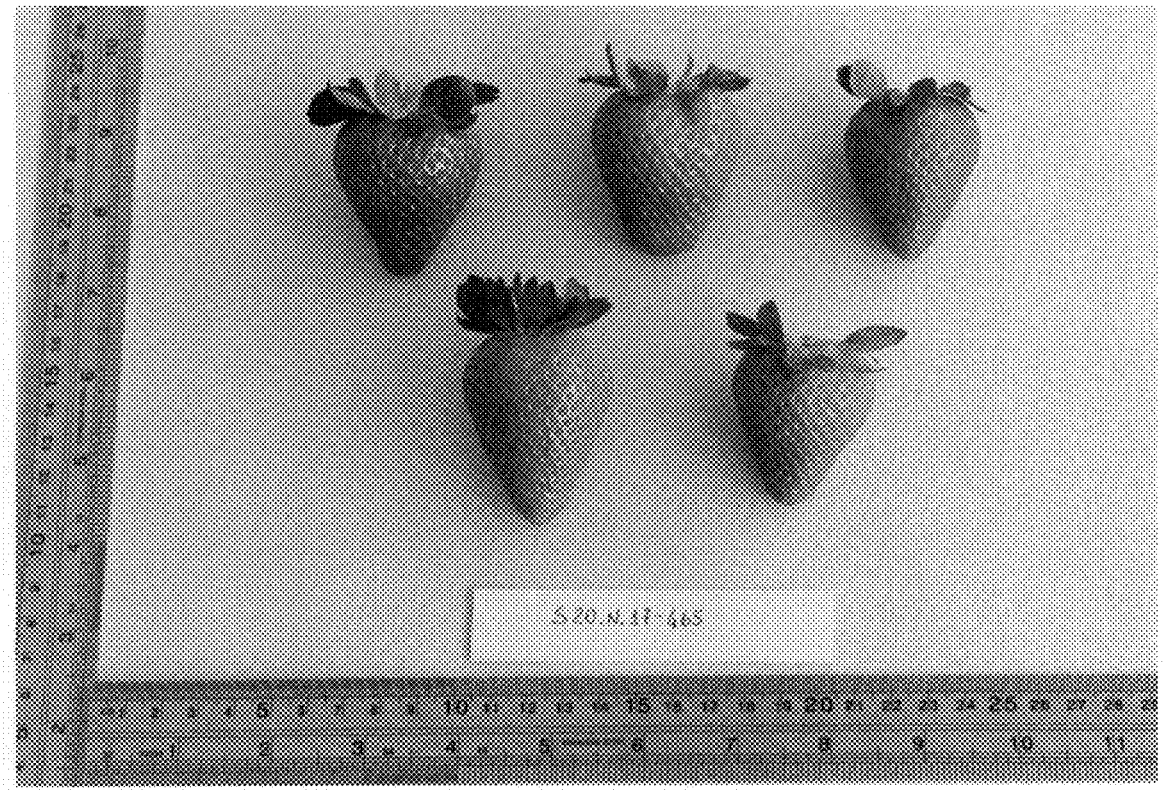

FIG. 10—illustrates specimens of the new variety's mature fruit—whole. Dimensions in centimeters and inches are included.

Figure 11:
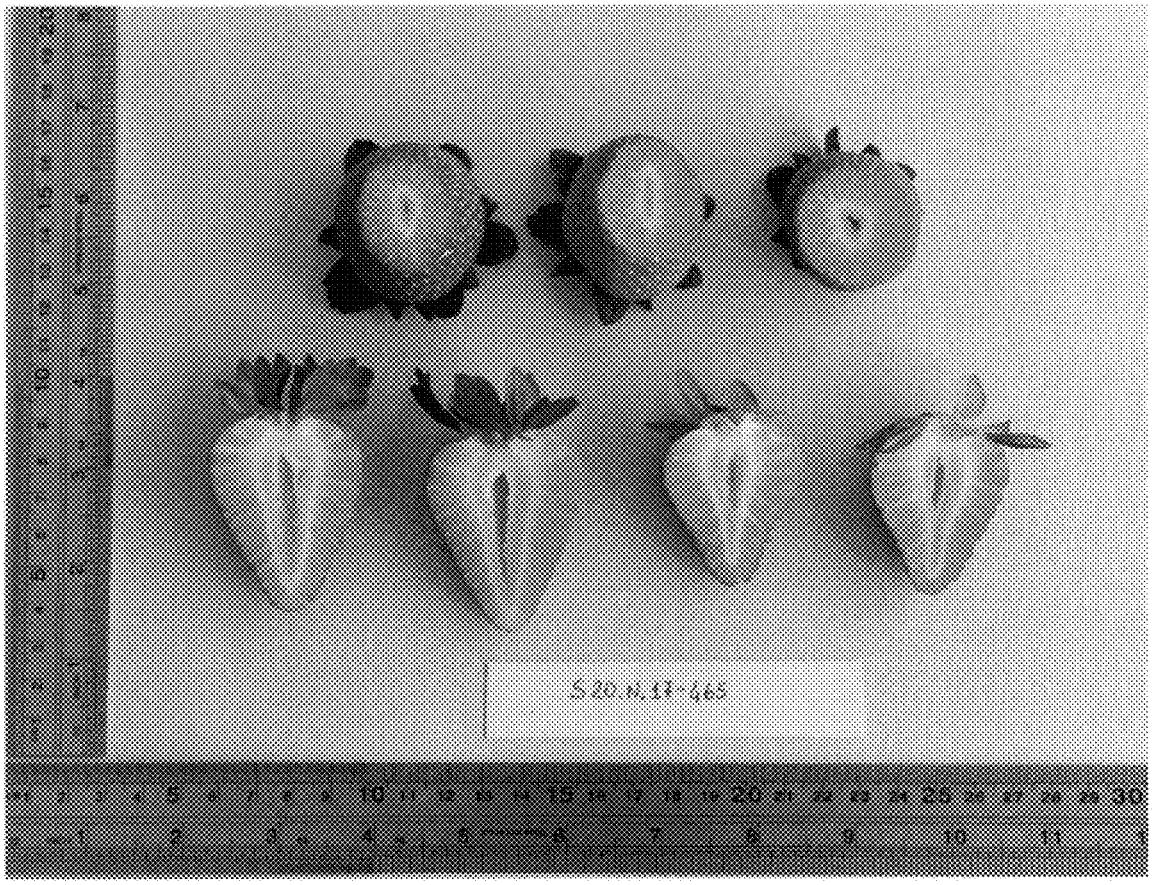

FIG. 11—illustrates specimens of the new variety's mature fruit—internal sections. Dimensions in centimeters and inches are included.

Figure 12:
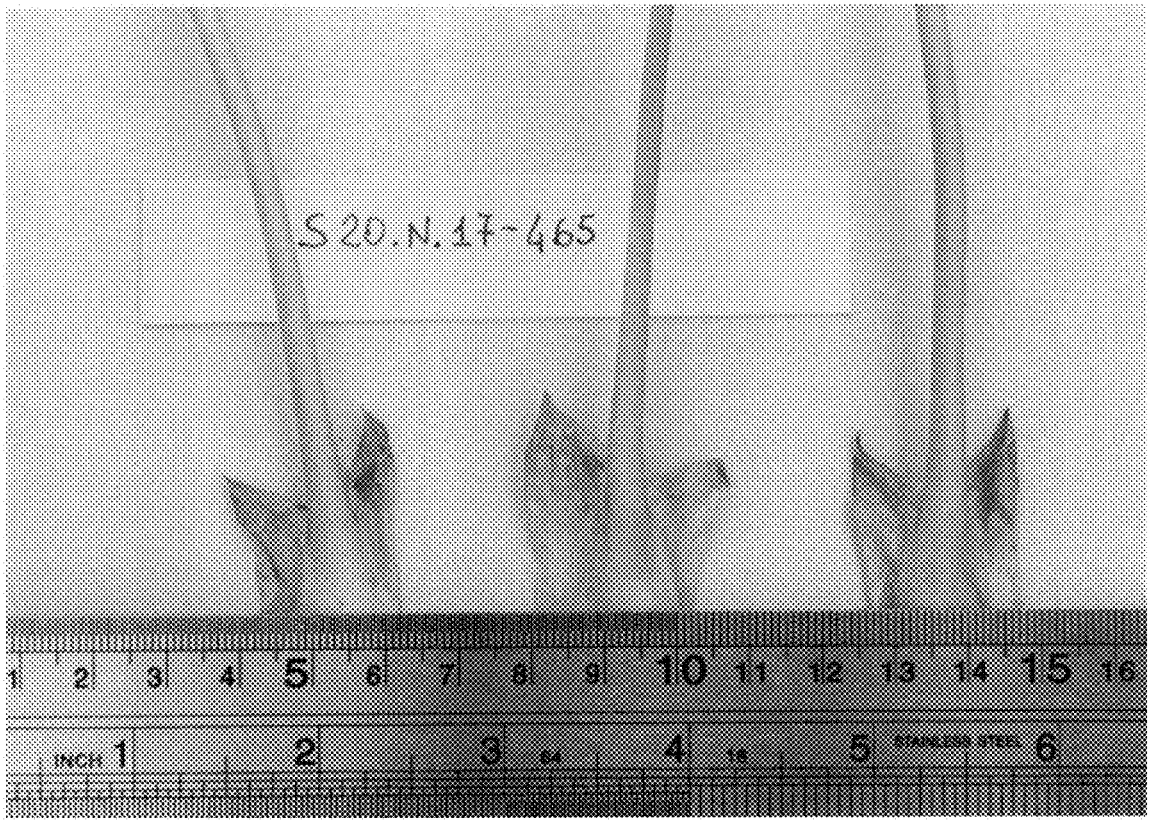

FIG. 12—illustrates specimens of the new variety's stipules—open. Dimensions in centimeters and inches are included.

DETAILED BOTANICAL DESCRIPTION

The chart used in the identification of colors is that of The Royal Horticultural Society ("R.H.S." Colour Chart), London, England, Edition V. The terminology which precedes reference to the chart has been added to indicate the corresponding color in more common terms. The detailed botanical description is based on plants which were reproduced asexually by the use of stolons in TORDESILLAS, Spain, located at 41° 494 N-4° 908 E, transplanted in Policoro (MT), Italy located at 40° 197 N-16° 656 E in October and grown under the cover of plastic tunnels.

The age of the plants on which the botanical description was made is between two and eight months from the transplants.

Plant:

*Type*.—Short-day.

*Configuration*.—Semi upright to spreading and semi-dense.

*Vigor*.—Medium.

*Spread*.—Sparse.

*Height* (*average*).—Approximately from 19 cm to 23 cm.

*Leaf*.—Length approximately from 23 cm to 26 cm, petiole and stipule included. — width approximately from 11 cm to 15 cm.

*Leaflets*.—Number: commonly 3. — terminal leaflet size: medium-to large in size, approximately 7 cm in length on average, and approximately 8 cm in width on average. — terminal leaflet: commonly equal in length and width, possesses a generally concave cross-section, possesses a crenate margin, and an obtuse base. — blistering: commonly is high in quantity. — glossiness on the upper surface: medium. — color: variegated coloration commonly is absent; upper surface coloration commonly being near Green Group 135A to Green Group 139A; and under surface commonly being near Green Group 138B to Green Group 138C. — texture (upper surface): wrinkled with small translucent waxy points and a medium presence of trichomes on the whole surface, with vertical orientation. — texture (lower surface): generally wrinkled with trichomes present, especially on the ribs. — venation pattern: the main transverse ribs are grafted forming an acute angle, at the insertion level of the main transverse rib there is no curvature in the initial part. At about half of the length it's possible to see a curvature. The first transverse ribs, close to the base of the insertion with the petiole, have an initial curvature. The tertiary ribs are quite clear on the inferior surface of the leaf. — Foliage: medium density

*Stolons*.—High in quantity, medium pubescence in density, color is commonly near Yellow-Green Group 144A to Yellow-Green Group 145B, weak anthocyanin coloration near Red-Purple Group 59C, and the distance between plants rooted in the same stolon is approximately 32 cm to 38 cm on average.

*Petioles*.—Approximately 16 cm to 19 cm in length on average, the average minor axis and the average major axis, measured at approximately 3 cm from the base of the stipule are approximately 0.3 cm and 0.4 cm, respectively, and color is commonly near Yellow-Green Group N144C, and commonly bear generally horizontally disposed fine pubescence.

*Stipules*.—Approximately 3.5 cm to 3.8 cm in length on average, the average width of closed stipules, measured at the base of the stipule, is approximately 1.2 cm, the average width of open stipules is approximately 2.6 cm, color is near Yellow-Green 145 B to Yellow-Green 145 C with some anthocyanin coloration of near Red-Purple Group 58B to Red-Purple Group 58C.

*Floral fragrance*.—Present.

Inflorescence:

*Flowering time*.—Medium, third/fourth week of December in Policoro (MT), Italy located at 40° 197 N-16° 656 E.

*Flower disposition*.—Same level of the foliage.

*Flower number*.—Medium, commonly 6 to 8.

*Pedicel hairs*.—Pubescence generally disposed upwards.

*Pedicel color*.—Commonly near Yellow-Green Group 144D.

*Pedicel length*.—The average length of the main and secondary pedicles measured from the base of the calyx is approximately 13 cm.

*Pedicel diameter*.—The diameter measured at approximately 2 cm from the calyx is approximately 0.26 cm.

*Flower size*.—Medium, with primary flowers approximately 2.5 cm to 3 cm in diameter on average, and secondary flowers approximately 2.1 cm to 2.4 cm in diameter on average. Commonly the open calyx is much larger than the diameter of the corolla, being approximately 4.2 cm to 4.6 cm in diameter on average.

*Petals*.—Number: approximately 5 to 7 on average, typically 6. — arrangement and shape: slightly overlapping, moderately longer in length than width. — size: approximately 1.1 cm on average in length and 1 cm in width on average. — color: near to White Group NN155B on the upper surface. — texture (upper surface): spongy texture, smooth, glabrous surface, with small translucent points; slight roughness at the level of insertion on the calyx. — texture (lower surface): weak general roughness, which become high at the insertion with the base. Glabrous surface.

*Stamens*.—Average number: approximately 29. — average length: approximately 0.3 cm to 0.4 cm. — filament color: Yellow-Green Group 150C.

*Anthers*.—Number is approximately 28 to 30 on average and color is commonly Yellow Group 12A.

*Pollen*.—In abundance. — color: close to yellow group 13A.

*Stigma*.—Shape: jagged fan shape. — size: an average opening at approximately 400 μm. — texture: waxed stigma, not feathery.

*Style*.—Average length: approximately between 1750 μm. — average diameter: approximately 220 μm, which thins at the level of the insertion on the ovary, entirely crossed by a stylus channel with an average diameter of approximately 50 μm. — shape: Gynobasic style.

*Ovary*.—Superior, with oval shape and average major axis and the average minor axis of approximately 690 μm and 460 μm.

*Sepals*.—Shape: generally lanceolate in configuration; attitude is commonly upwards, and generally extend beyond the petals. — number: approximately 9 to 13 on average. — size: approximately 2 cm to 2.5 cm in length on average, and approximately 0.8 cm to 1.2 cm in width on average at the broadest point. — color: the upper surface is commonly near Green Group 141A and the under surface is commonly near Green Group 139C to Green Group 139D. — texture (upper surface): slightly wrinkled with trichomes and translucent waxy points on the whole surface. — texture (lower surface): slightly wrinkled with trichomes present on the whole surface and on the borders. On the fully developed sepals there's a high density of trichomes on the apical part.

Fruit:

*Bearing*.—Non-remontant.

*Timing*.—Medium fruiting commonly with approximately 32 to 38 days from first blooming to first fruit ripening.

*Shape*.—Conical, moderately longer than broad, commonly with a slight difference between terminal and the other fruits.

*Size*.—Large, with the primary fruit approximately 5.6 cm to 6.3 cm in length on average; approximately 4.6 cm to 5.2 cm in width on average at the broadest point; and approximately 26 grams on average.

*Surface*.—Generally smooth with strong glossiness.

*External color*.—Substantially uniform, commonly near Red Group 46B to Red Group 45B.

*Internal color*.—The flesh and the core are commonly near Orange-Red Group 33A (flesh) and 33B (core).

*Firmness*.—Very good firmness.

*Cavity*.—Medium fruit cavity, as illustrated in FIG. 11.

*Achenes*.—Located generally below the fruit surface and cover nearly the entire fruit surface commonly with only a very narrow band (if any) where achenes are absent, and commonly going from near Red Group 45A to Red Group 45B in coloration, depending of fruit maturity.

*Calyx*.—Commonly on the same level of the fruit at the point of attachment, the calyx commonly attaches to the fruit with medium to weak adherence, the sepals are disposed generally upwards and the fruit diameter of calyx in relation to diameter of fruit commonly are much bigger.

*Peduncle*.—Medium length, elliptical shaped in section, with the average length of the primary peduncle, measured from the base of the calyx of the primary fruit, approximately from 15 cm to 18 cm, average minor axis and the average major axis are approximately 0.4 cm and 0.5 cm respectively. The diameters of the axis are measured at approximately 3 cm from the base of the peduncle from which secondary and primary peduncles begins. The peduncle measured includes the pedicel that carries the main mature fruit and in addition the underlying peduncle. The color is commonly near Yellow-Green Group N144B.

*Pedicel*.—Commonly with pubescence extending upwards, and color is commonly near Yellow-Green Group N144D.

*Storability*.—Medium to high.

*Shipping quality*.—Medium-high.

*Market use*.—Fresh.

Development:

*Fertilization*.—Self-fertile.

*Resistance to disease*.—During the time of observations and to date, no sensitivities to any disease were observed.

*Winter hardiness/cold tolerance*.—Unknown.

*Drought/heat tolerance*.—Good.

Plants of the 'NSG 465' variety have not been observed under all possible environmental conditions to date. Accordingly, it is possible that the phenotypic expression may vary somewhat with changes in light intensity and duration, cultural practices, and other environmental conditions.

SUPPLEMENTAL COMPARATIVE DATA

Hereafter, additional comparative fruit data is provided for the new variety: the 'NSG 465' variety, the 'SIRIS' variety (i.e., the female parent), the 'NSG 120' variety (i.e., the male parent) and the 'NSG 207' variety. The plants were asexually reproduced by the use of stolons in 2021 in TORDESILLAS, Spain located at 41° 494 N-4° 908 E, and planted in field on October 18, 2021. All varieties were grown under the cover of plastic tunnels in Policoro (MT), Italy located at 40° 197 N-16° 656 E. The first pick of the fruit occurred on Jan. 22, 2022 and the last pick of the fruit occurred on May 16, 2022. The fruit were evaluated and compared on the dates indicated. Average data are followed:

TABLE 1

Accumulated Production of First Quality Fruit (g/plant)

| Variety | February 28$^{th}$ | March 30$^{th}$ | April 30$^{th}$ | May 16$^{th}$ |
|---|---|---|---|---|
| 'NSG 465' | 14 | 160 | 406 | 620 |
| 'NSG 207' | 81 | 256 | 466 | 580 |

TABLE 2

Overall Comparison of Average Fruit Weight in Policoro - Italy on year 2022

| Variety | g/fruit |
|---|---|
| 'NSG 465' | 26 |
| 'SIRIS' | 21 |
| 'NSG 120' | 21 |
| 'NSG 207' | 24 |

TABLE 3

Average Fruit Weight on Specified Dates in 2022

| Variety | March 30$^{th}$ (grams) | April 30$^{th}$ (grams) | May 16$^{th}$ (grams) |
|---|---|---|---|
| 'NSG 465' | 27 | 25 | 26 |
| 'SIRIS' | 22 | 20 | 21 |
| 'NSG 120' | 22 | 22 | 19 |
| 'NSG 207' | 26 | 24 | 22 |

TABLE 4

Fruit Analysis on May 4, 2022

| | 'NSG 465' | 'NSG 207' | 'NSG120' | 'SIRIS' |
|---|---|---|---|---|
| Firmness (average)* | 0,72 | 0.60 | 0.57 | 0.67 |
| Dry Matter (%)** | 8.72 | 7.8 | 9.85 | 9.61 |
| pH (to 20°) | 3.67 | 3.59 | 3.55 | 3.69 |
| Acidity as Anhydride Citric (%) | 0.48 | 0.51 | 0,48 | 0.46 |
| Soluble Solids (% Brix) | 8.50 | 8.50 | 10 | 10 |
| Maturity Index*** | 17.8 | 16.8 | 20.9 | 21.6 |

*Resistance to penetration measured in kilograms using a Turoni (Italy) penetrometer (20 Kg × 0.01).
**Ratio ISTISAN 1996/34 pg. 7 METHOD B.
***MIP 160 2013 Rev. 0.

I claim:

1. A new and distinct variety of strawberry plant named 'NSG 465', as illustrated and described herein.

* * * * *